United States Patent
Hagen et al.

(10) Patent No.: US 9,171,279 B2
(45) Date of Patent: *Oct. 27, 2015

(54) RECEPTACLE RACK HAVING AN ELECTRONIC MEMORY ELEMENT

(71) Applicant: GEN-PROBE INCORPORATED, San Diego, CA (US)

(72) Inventors: Norbert D. Hagen, Carlsbad, CA (US); David Opalsky, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/195,718

(22) Filed: Mar. 3, 2014

(65) Prior Publication Data

US 2014/0175168 A1  Jun. 26, 2014

Related U.S. Application Data

(63) Continuation of application No. 13/293,529, filed on Nov. 10, 2011, now Pat. No. 8,662,392.

(60) Provisional application No. 61/413,050, filed on Nov. 12, 2010.

(51) Int. Cl.
  *G06F 19/00*  (2011.01)
  *G06Q 10/08*  (2012.01)
  *G01N 35/00*  (2006.01)

(52) U.S. Cl.
  CPC ........ *G06Q 10/087* (2013.01); *G01N 35/00732* (2013.01); *G01N 2035/00752* (2013.01);
  (Continued)

(58) Field of Classification Search
  USPC .................................. 235/385, 375
  See application file for complete search history.

(56) References Cited

U.S. PATENT DOCUMENTS

| 5,314,825 A | 5/1994 | Weyrauch et al. |
| 5,672,317 A | 9/1997 | Bühler et al. |

(Continued)

FOREIGN PATENT DOCUMENTS

| CN | 1739856 A | 3/2006 |
| EP | 0979999 A2 | 2/2000 |

(Continued)

OTHER PUBLICATIONS

SIPO Office Action, Chinese Patent Application No. 201180054611.9, Jan. 30, 2014.

(Continued)

*Primary Examiner* — Ahshik Kim
(74) *Attorney, Agent, or Firm* — Charles B. Cappellari; Richard Wydeven

(57) ABSTRACT

A system and method for tracking items, such as receptacles, during a process employs a rack configured to hold one or more receptacles. Each receptacle includes a machine-readable label providing information regarding the receptacle, such as contents thereof and process(es) to be performed thereon, and each receptacle-receiving position of the rack has associated therewith a machine-readable label identifying the receptacle receiving location. The rack also includes a memory element to which electronic data may be written. A label reading device reads the machine-readable label on each receptacle and the position-indicating, machine-readable labels on the rack. Information obtained from the machine-readable labels is written to the memory element, so that for subsequent processing of the receptacles carried on the rack, information relating to each of the receptacles can be obtained by reading the information written to the memory element. A tamper prevention element provides an indication of whether the rack may have been tampered with after data is written to the memory element.

13 Claims, 13 Drawing Sheets

(52) U.S. Cl.
CPC ............... *G01N2035/00782* (2013.01); *G01N 2035/00801* (2013.01); *G01N 2035/00831* (2013.01); *G01N 2035/00841* (2013.01)

(56) References Cited

U.S. PATENT DOCUMENTS

| | | | |
|---|---|---|---|
| 5,700,429 | A | 12/1997 | Bühler et al. |
| 5,861,563 | A | 1/1999 | Boyd et al. |
| 6,060,022 | A | 5/2000 | Pang et al. |
| 6,086,824 | A | 7/2000 | Fanning et al. |
| 6,197,260 | B1 | 3/2001 | Bradshaw et al. |
| 6,426,044 | B1 | 7/2002 | Cohen et al. |
| 7,278,328 | B2 | 10/2007 | Massaro |
| 7,282,182 | B2 | 10/2007 | Dale et al. |
| 7,504,949 | B1 | 3/2009 | Rouaix et al. |
| 7,910,067 | B2 | 3/2011 | Knight et al. |
| 7,931,201 | B2 | 4/2011 | Zhang et al. |
| 8,394,635 | B2 | 3/2013 | Key et al. |
| 8,662,392 | B2 * | 3/2014 | Hagen et al. ............. 235/385 |
| 2004/0005714 | A1 | 1/2004 | Safar et al. |
| 2004/0092025 | A1 | 5/2004 | Mordekhay |
| 2004/0195193 | A1 | 10/2004 | Jafari et al. |
| 2005/0205673 | A1 | 9/2005 | Morris et al. |
| 2006/0051239 | A1 | 3/2006 | Massaro |
| 2006/0190185 | A1 | 8/2006 | Ford et al. |
| 2006/0266719 | A1 | 11/2006 | Knight et al. |
| 2008/0014118 | A1 | 1/2008 | Kitagawa et al. |
| 2008/0042839 | A1 | 2/2008 | Grater et al. |
| 2009/0136386 | A1 | 5/2009 | Duffy et al. |
| 2009/0220379 | A1 | 9/2009 | Wakamiya et al. |
| 2010/0021352 | A1 | 1/2010 | Trueeb et al. |
| 2010/0126286 | A1 | 5/2010 | Self et al. |
| 2012/0145798 | A1 | 6/2012 | Morris et al. |
| 2012/0258463 | A1 | 10/2012 | Duffy et al. |

FOREIGN PATENT DOCUMENTS

| | | | |
|---|---|---|---|
| EP | 1447669 | A2 | 8/2004 |
| EP | 1447669 | A3 | 8/2004 |
| EP | 2 000 211 | A1 | 12/2008 |
| EP | 2073017 | A1 | 6/2009 |
| EP | 2080553 | A1 | 7/2009 |
| JP | 8-292194 | A | 11/1996 |
| JP | 11-242036 | A | 9/1999 |
| JP | 2004-93518 | A | 3/2004 |
| JP | 2005-17177 | A | 1/2005 |
| JP | 2008-64586 | A | 3/2008 |
| JP | 2008-537147 | A | 9/2008 |
| WO | 94/01781 | A1 | 1/1994 |
| WO | 03/008099 | A2 | 1/2003 |
| WO | 03/008099 | A3 | 1/2003 |
| WO | 03/097240 | A2 | 11/2003 |
| WO | 2005/093433 | A1 | 10/2005 |
| WO | WO2006/113854 | A2 | 10/2006 |
| WO | 2007/121324 | A1 | 10/2007 |
| WO | 2008/044594 | A1 | 4/2008 |

OTHER PUBLICATIONS

International Search Report and Written Opinion in PCT/2010/035146, 20 pages, mailed Dec. 27, 2010.
International Search Report and Written Opinion, International Application No. PCT/US2011/060159, mailed Feb. 9, 2012.
Non-final Office Action, U.S. Appl. No. 13/293,529, mailed Jan. 30, 2013.
Final Rejection, U.S. Appl. No. 13/293,529, mailed Jul. 5, 2013.
Notice of Allowance, U.S. Appl. No. 13/293,529, mailed Oct. 16, 2013.
IP Australia Office Action, Australian Patent Application No. 2011326484, Dec. 17, 2013.
CIPO, Office Action, Canadian Patent Application No. 2,817,101, Nov. 27, 2014.
SIPO, Office Action, Chinese Patent Application No. 201180054611.9, Jan. 12, 2015.
SIPO, Supplementary Search Report, Chinese Patent Application No. 201180054611.9, Jan. 12, 2015.
JPO, Office Action, Japanese Patent Application No. 2013-538880, Jul. 22, 2015.

* cited by examiner

RECEPTACLE RACK HAVING AN ELECTRONIC MEMORY ELEMENT

CROSS-REFERENCE TO RELATED APPLICATIONS

This application is a continuation under 35 U.S.C. §120 of U.S. application Ser. No. 13/293,529, filed Nov. 10, 2011, now U.S. Pat. No. 8,662,392, which claims the benefit under 35 U.S.C. §119(e) of U.S. Provisional Application No. 61/413,050, filed Nov. 12, 2010, the disclosures of which applications are hereby incorporated by reference in their entirety.

BACKGROUND

1. Field of the Invention

This invention relates to systems, methods, and apparatus for storing and presenting sample materials for access by a sample transfer apparatus and for limiting the incidence of cross-contamination between sample-containing vessels during a sample transfer operation.

2. Background of the Invention

All documents referred to herein, or the indicated portions, are hereby incorporated by reference herein. No document, however, is admitted to be prior art to the claimed subject matter.

Analyzers for performing assays on fluid samples typically include a fluid transfer mechanism for transferring fluid sample material and other fluids between various receptacles or containers. For example, fluid sample material may be introduced into the analyzer via a sample receptacle, such as a test tube containing an amount of the fluid sample, placed in the analyzer or in operative proximity to the analyzer. The analyzer may include an automated fluid transfer mechanism comprising a robotically-controlled pipetting device having an aspirating probe for accessing the contents of a receptacle. The probe may comprises a barrel with a protective tip (e.g., a pipette tip) mounted (e.g., frictionally) on its distal end.

Fluid sample material is transferred from the sample receptacle by positioning the aspirating probe above the sample receptacle and then lowering the probe until a distal end of the probe is submerged in the fluid sample material held in the container. After the probe is submerged, an amount of fluid is drawn into the probe. The probe is then raised and moved to another location within the analyzer and is operatively positioned above another container (or, alternatively, the probe can be held in a fixed position and the sample receptacle and other containers can be moved relative to the probe). The sample material may be transferred to a reaction receptacle (e.g., test tube, cuvette, microtiter plate well, etc.) within which the sample material is combined with reagents and/or other reactants (and, optionally, the container and its contents may be subjected to other conditions or stimuli, such as, incubation at an elevated temperature, mixing, and/or centrifuging) to effect a transformation or chemical, biochemical or biological reaction. After the probe is positioned above the container that is to receive the sample material, some or all of the fluid is dispensed from the probe into one or more containers, moving the probe from receiving container to receiving container as necessary.

During such a fluid transfer procedure, care must be taken to avoid cross-contamination due to spilled or misplaced sample material. For example, sample from one sample receptacle should not be mistakenly deposited into another sample receptacle containing a different sample or a sample from a different source. Similarly, no sample material should be deposited into a reaction receptacle in which such sample is not intended, for example in a reaction receptacle within which a different sample had already been dispensed.

SUMMARY OF THE INVENTION

Aspects of the invention are embodied in a receptacle rack configured to hold a plurality of receptacles. The receptacle rack includes receptacle holding structure defining a plurality of receptacle-receiving pockets, machine-readable position data associated with each receptacle-receiving pocket, and an electronic memory element. Each of the pockets is configured to receive and hold a receptacle. The machine-readable position data is associated with each receptacle-receiving pocket and includes information relating to a position of each receptacle-receiving pocket. The electronic memory element is configured to store information relating to receptacles held within receptacle-receiving pockets of the receptacle rack and the information relating to a position of each receptacle-receiving pocket.

According to another aspect of the invention embodied in the receptacle rack, the receptacle rack further includes at least one receptacle held within a receptacle-receiving pocket, and the receptacle includes machine-readable receptacle data comprising information relating to the contents of the receptacle.

According to another aspect of the invention embodied in the receptacle rack, the machine-readable receptacle data comprises a bar code disposed on the receptacle.

According to another aspect of the invention embodied in the receptacle rack, the machine-readable position data comprises a bar code disposed adjacent to each receptacle-receiving pocket.

According to another aspect of the invention embodied in the receptacle rack, the memory element comprises a radio frequency identification (RFID) tag.

According to another aspect of the invention embodied in the receptacle rack, the memory element comprises a touch memory element.

According to another aspect of the invention embodied in the receptacle rack, the receptacle rack further comprises a cover configured to be removably secured to the receptacle-holding structure so as to cover any receptacle(s) held within receptacle-receiving pockets defined by the receptacle-holding structure and a tamper prevention element configured to indicate if a cover that is secured to the receptacle-holding structure while information is being stored on the electronic memory element has been removed from the receptacle-holding structure after the information is stored on the electronic memory element.

According to another aspect of the invention embodied in the receptacle rack, the tamper-prevention element comprises an indicator element that is alterable between a first configuration when the cover is secured to the receptacle-holding structure while information is being stored on the electronic memory element and a second configuration when the cover is removed from the receptacle-holding structure after the information is stored on the electronic memory element.

According to another aspect of the invention embodied in the receptacle rack, the indicator element comprises a movable flag mounted on the cover or the receptacle holding structure to be movable between a locked position and an unlocked position.

According to another aspect of the invention embodied in the receptacle rack, the indicator element further comprises a flag biasing element and flag holding structure. The flag biasing element is configured to bias the flag into its unlocked position. The flag holding structure is configured to hold the flag in its locked position while the cover is secured to the receptacle-holding structure and is configured such that it will no longer hold the flag in its locked position if the cover is removed from the receptacle-holding structure so that the flag biasing element will cause the flag to return to its unlocked position.

According to another aspect of the invention embodied in the receptacle rack, the machine-readable receptacle data comprises information identifying a sample material contained in the receptacle.

According to another aspect of the invention embodied in the receptacle rack, the machine-readable receptacle data comprises information identifying a reagent contained in the receptacle.

Other aspects of the invention are embodied in a method for reading machine-readable labels disposed on receptacles carried on a receptacle rack, reading machine-readable labels disposed on the rack, and writing data relating to the receptacles and the positions of the receptacles to a memory element on the rack. A rack holding at least one receptacle having a machine-readable label disposed thereon is placed in a rack-receiving location. During or after placing the rack in the rack-receiving location, a machine-readable label of each receptacle is read with a label reading device to obtain receptacle data for each receptacle, and receptacle position-identifying labels disposed on the rack are read with the label reading device to obtain receptacle position data for each receptacle. The data writing device is then used to write the receptacle data and the corresponding receptacle position data for each receptacle to the memory element.

According to another aspect of the invention embodied in the method, the label reading device comprises at least one bar code reader held in a fixed position with respect to the rack-receiving location.

According to another aspect of the invention embodied in the method, the machine-readable label disposed on each receptacle comprises a receptacle bar code.

According to another aspect of the invention embodied in the method, the position-identifying labels disposed on the rack comprise position bar codes disposed adjacent to each receptacle-receiving location of the rack.

According to another aspect of the invention embodied in the method, the memory element comprises an RFID tag.

According to another aspect of the invention embodied in the method, the memory element comprises a touch memory element.

According to another aspect of the invention embodied in the method, the label reading device comprises a bar code reader held in a fixed position with respect to the rack-receiving location, the machine-readable label disposed on each receptacle comprises a receptacle bar code, the position-identifying labels disposed on the rack comprise position bar codes disposed adjacent to each receptacle-receiving location of the rack, and reading the machine-readable label of each receptacle comprises moving the rack relative to the bar code reader and reading each receptacle bar code and each position bar code as it passes the bar code reader.

According to another aspect of the invention embodied in the method, the method further comprises the step of determining if a cover disposed over receptacles held on a rack while data is being written to the memory element has been removed after data has been written to the memory element.

According to another aspect of the invention embodied in the method, determining if a cover has been removed is performed with a tamper-prevention element comprising a movable flag mounted on the cover or the rack to be movable between a locked position and an unlocked position.

According to another aspect of the invention embodied in the method, the tamper-prevention element further comprises a flag biasing element and a flag holding structure. The flag biasing element is configured to bias the flag into its unlocked position. The flag holding structure is configured to hold the flag in its locked position while the cover is secured to the rack, and the flag holding structure is configured such that it will no longer hold the flag in its locked position if the cover is removed from the rack so that the flag biasing element will cause the flag to return to its unlocked position.

Other aspects of the invention are embodied in a system for tracking reaction receptacles during a process in which the system comprises a receptacle rack, a first rack-receiving location, a label reading device, a data writing device, a second rack-receiving location, and a data reading device. The receptacle rack is configured to hold a plurality of receptacles and comprises receptacle holding structure defining a plurality of receptacle-receiving pockets, each configured to receive and hold a receptacle and a memory element configured to store data. The first rack-receiving location is configured to receive the receptacle rack holding the one or more receptacles, and the label reading device is operatively disposed with respect to the first rack-receiving location and configured to read machine-readable data disposed on the receptacle rack and/or on one or more receptacles held on the rack when the rack is placed in the first rack-receiving location. The data writing device is operatively disposed with respect to the first rack-receiving location and configured to write the data read by the label reading device to the memory element of the receptacle rack placed in the first rack-receiving location. The second rack-receiving location is configured to receive the receptacle rack holding the one or more receptacles, and the data reading device is operatively disposed with respect to the second rack-receiving location and configured to read data stored on the memory element of the receptacle rack placed in the second rack-receiving location.

According to another aspect of the invention embodied in the system, the system further comprises machine-readable position data disposed on the receptacle rack and associated with each receptacle-receiving pocket and including information relating to a position of each receptacle-receiving pocket and one or more receptacles, each receptacle being disposed in one of the receptacle-receiving pockets of the receptacle rack and including machine-readable receptacle data. The label reading device is configured to read machine-readable position data disposed on the receptacle rack and the machine-readable receptacle data on the receptacles held on the rack when or while the rack is placed in the first rack-receiving location, and the data writing device is configured to write data relating to the receptacle data and the corresponding receptacle position data for each receptacle to the memory element of the receptacle rack placed in the first rack-receiving location.

According to another aspect of the invention embodied in the system, the system further comprises data storage including information relating to the contents of each receptacle and associated with the machine-readable receptacle data of each receptacle.

According to another aspect of the invention embodied in the system, the machine-readable receptacle data comprises a bar code disposed on the receptacle, and the label reading device comprises a bar code reader.

According to another aspect of the invention embodied in the system, the machine-readable position data comprises a bar code disposed adjacent to each receptacle-receiving pocket, and the label reading device comprises a bar code reader.

According to another aspect of the invention embodied in the system, the memory element comprises an RFID tag.

According to another aspect of the invention embodied in the system, the memory element comprises a touch memory element.

According to another aspect of the invention embodied in the system, the receptacle rack further comprises a cover configured to be removably secured to the receptacle-holding structure so as to cover any receptacle(s) held within receptacle-receiving pockets of the receptacle rack and a tamper prevention element configured to indicate if a cover that is secured to the receptacle-holding structure while data is being written to the memory element by the data writing device has been removed from the receptacle-holding structure after data has been written to the memory element by the data writing device.

According to another aspect of the invention embodied in the system, the system further comprises a computer controller configured to reject data read by said data reading device if the tamper prevention element indicates the cover has been removed after having been initially secured to the receptacle-holding structure.

According to another aspect of the invention embodied in the system, the machine-readable receptacle data relates to information identifying a sample material contained in the receptacle.

According to another aspect of the invention embodied in the system, the machine-readable receptacle data relates to information identifying a reagent contained in the receptacle.

According to another aspect of the invention embodied in the system, the first rack-receiving location is a stand-alone module.

According to another aspect of the invention embodied in the system, the first rack-receiving location is integral with an instrument configured to process the contents of the receptacle.

According to another aspect of the invention embodied in the system, the system further includes a tamper prevention element comprising a movable flag mounted on the cover or the receptacle holding structure to be movable between a locked position and an unlocked position.

According to another aspect of the invention embodied in the system, the tamper prevention element further comprises a flag biasing element, a flag engaging element, and flag holding structure. The flag biasing element is configured to bias the flag into its unlocked position. The flag engaging element is associated with the first rack-receiving location and is configured to move the flag from the unlocked position to the locked position when the receptacle rack with a cover secured to the receptacle-holding structure is placed in the first rack-receiving location. The flag holding structure is configured to hold the flag in its locked position after the flag engaging element has moved the flag to the locked position while the cover is secured to the receptacle-holding structure. The flag holding structure is configured such that it will no longer hold the flag in its locked position if the cover is removed from the receptacle holding-structure so that the flag biasing element will cause the flag to return to its unlocked position.

According to another aspect of the invention embodied in the system, the tamper prevention element further comprises a flag position detection element associated with the second rack-receiving location and configured to detect if the flag is in the locked position when the rack is placed in the second rack-receiving location.

These and other features, aspects, and advantages of the present invention will become apparent to those skilled in the art after considering the following detailed description, appended claims and accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF THE INVENTION

Figure 1:
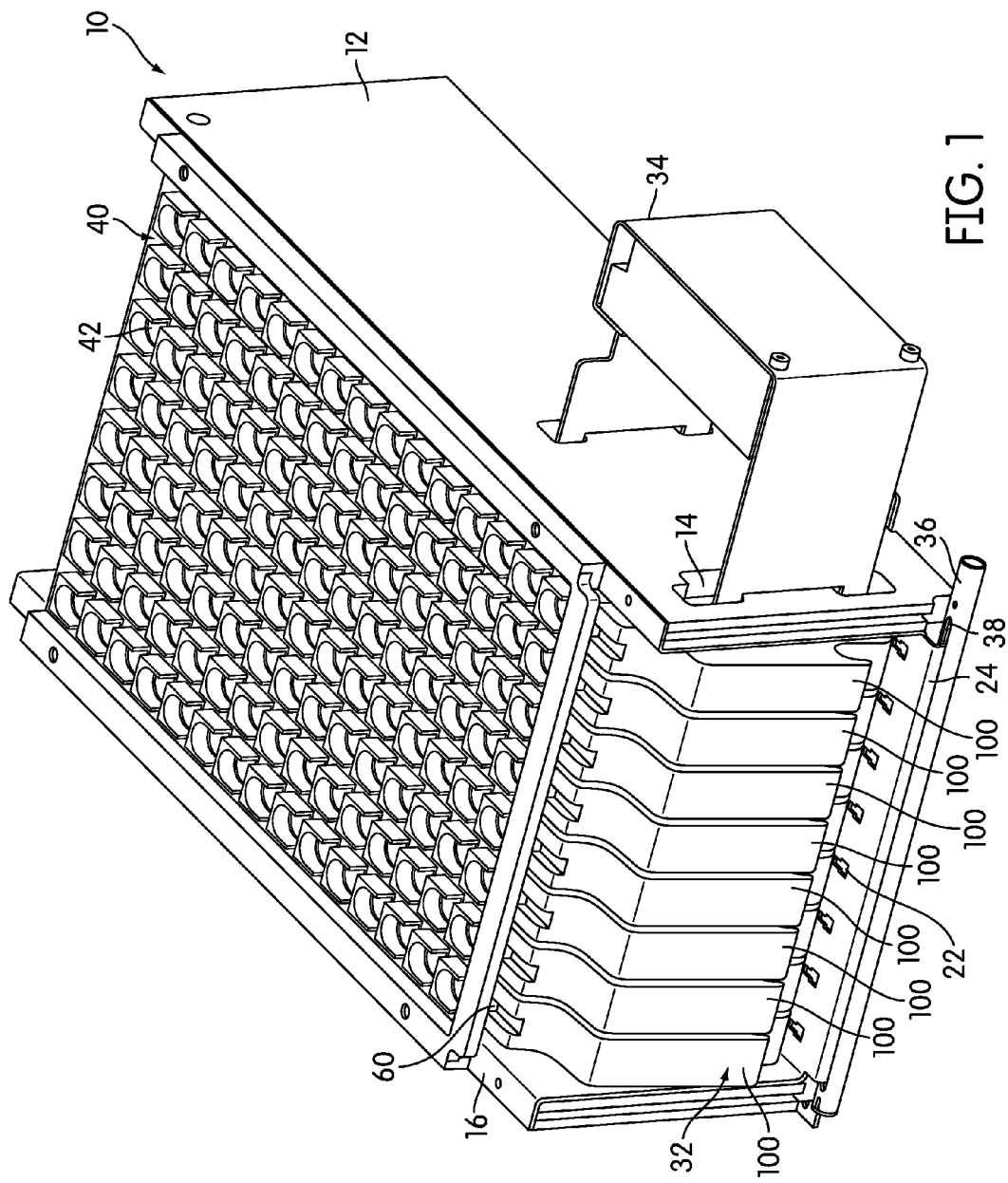
FIG. 1 is an upper front perspective view of a sample receptacle module embodying aspects of the present invention.

As shown in FIG. 1, a sample receptacle module embodying aspects of the present invention includes a sample bay 10 within which are disposed a plurality of sample racks 100. In the illustrated embodiment, the sample bay 10 holds up to eight sample racks 100.

Figure 2:
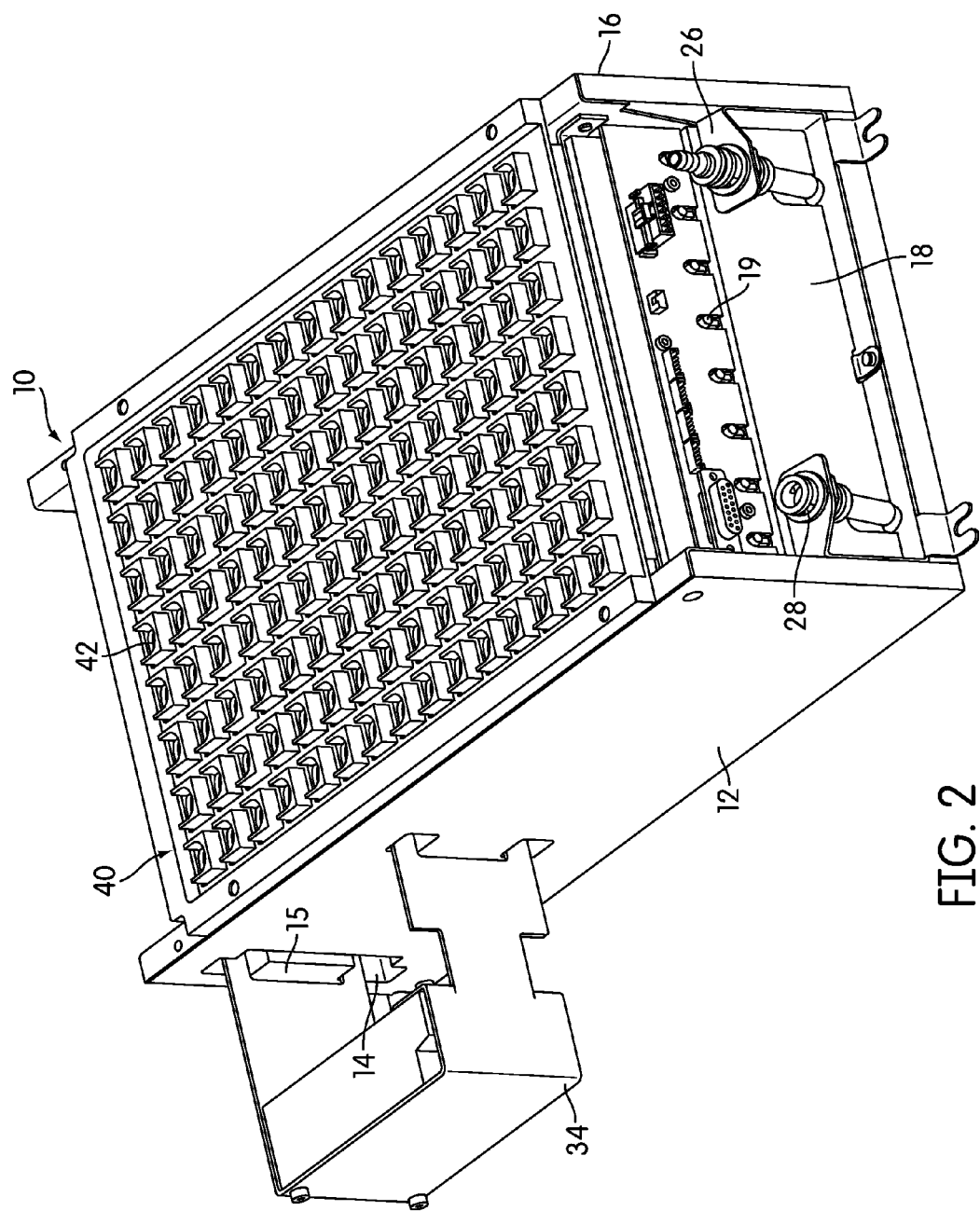
FIG. 2 is an upper rear perspective view of the sample receptacle module.
Figure 3:
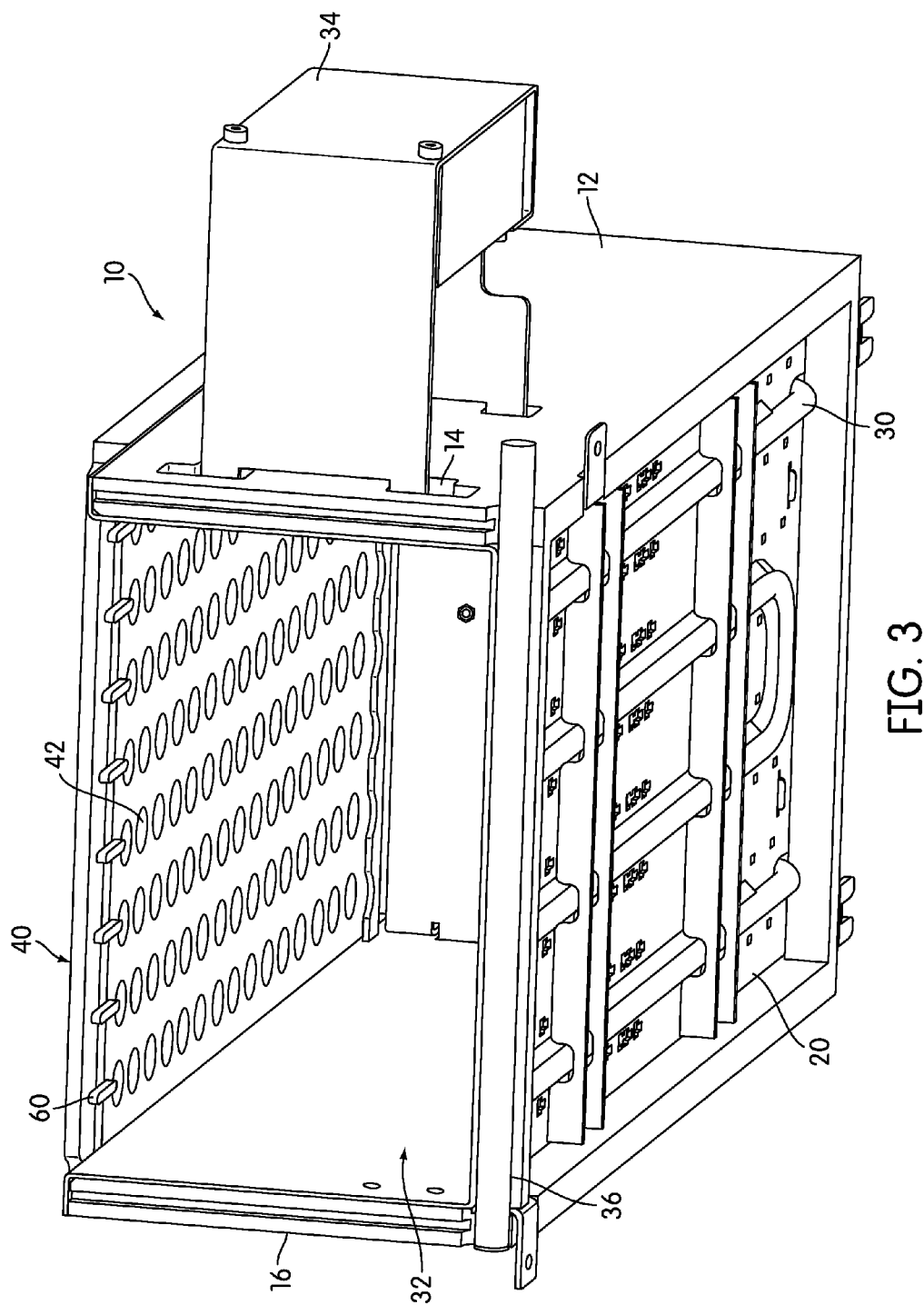
FIG. 3 is a lower front perspective view of a sample bay of the sample receptacle module.

As shown in FIGS. 1-3, the sample bay 10 is a box-like structure having a first side wall 12, a second side wall 16, a back wall 18, and a floor plate 20. The walls 12, 16, and 18 may be thermally insulated. The sample bay 10 further includes a sample bay cover 40 carried at its edges by the walls 12, 16, and 18. A front end 32 of the sample bay 10 is open to permit the sample racks 100 to be inserted into and removed from the sample bay 10. The floor plate 20 may further include sample rack guides 22 which engage mating guides formed in the bottom of each sample rack 100 for accurately and repeatably positioning each rack. Holes 19 formed in back wall 18 are aligned with each sample rack position.

An embodiment of the sample bay 10 further includes a barcode bracket 34, which may be mounted to the first side wall 12 and configured to carry a barcode reader 15 in an operative position with respect to a barcode window 14 formed in the first side wall 12. The barcode reader 15 carried in the barcode bracket 34 is configured to read barcodes placed on individual sample receptacles carried in each of the sample racks 100 as well as barcodes on the sample racks 100 themselves. The barcodes are read through the barcode window 14 as the sample rack is pushed into or removed from the sample bay 10. A procedure for reading the barcodes on sample receptacles will be described below.

In one embodiment, the interior of the sample bay 10 is preferably kept at a cooler than ambient temperature by means of a coolant medium flowing through a coolant tube 30 arranged beneath the floor plate 20, as shown in FIG. 3. The coolant medium, which may comprise chilled water, is passed through the coolant tube 30 via a coolant inlet connector 28 and a coolant outlet connector 26 mounted behind the back wall 18, as shown in FIG. 2. Other cooling means, such as one or more thermoelectric Peltier devices, may be employed in addition to or as an alternative to coolant tube 30.

The chilled interior of the sample bay 10 can cause an accumulation of condensation inside the sample bay 10. To convey accumulated water away from the sample bay 10, a condensation tube 36 may be provided along the lower front edge of the front opening 32. The condensation tube 36 includes a top longitudinal slot 38, and a front edge 24 of the floor plate 20 is bent into the slot 38 to direct excess condensation collected on the floor plate 20 into the condensation tube 36. Condensation tube 36 conveys the collected condensation to a remote container or drain (not shown).

The sample bay cover 40 has formed therein a plurality of sample receptacle access openings 42, which, in the illustrated embodiment, are arranged in a rectangular array of rows and columns, each column of openings aligning with the position of a sample rack 100.

The sample rack 100 is shown in further detail in FIGS. 4-7. Sample rack 100 is adapted to receive and hold a plurality of receptacles, which, in certain embodiments, may comprise tubular containers, such as test tubes. Sample rack 100 includes a receptacle holder 102 and a cover 130. The receptacle holder 102 includes a handle 104 for grasping and carrying the receptacle holder 102 and for inserting the receptacle holder 102 into or removing the receptacle holder 102 from the sample bay 10. In one embodiment, a machine-readable label, such as a barcode 103, is provided on the receptacle holder 102, such as near the handle 104 as shown.

The receptacle holder 102 may be made from a suitable, non-reactive material, such as plastic or Delrin® acetyl resin, and includes a base 106 extending longitudinally from the handle 104. A guide track 108 (see FIG. 4) is formed in the base 106 for engaging the sample rack guides 22 provided in the floor plate 20 of the sample bay 10 to ensure proper positioning of the sample rack 100 within the sample bay 10. An embodiment of the receptacle holder 102 includes an alignment slot 118 formed in a top edge above the handle 104. Alignment slot 118 engages one of the alignment projections 60 formed along the bottom of a front edge of the sample bay cover 40 (See FIG. 3). A plurality of vertically oriented divider walls 110 extend upwardly, at spaced intervals, from the base 106. In the illustrated embodiment, the upper portions of the divider walls 110 are held in fixed relative positions by a side panel 122 extending longitudinally from the handle 104 to an end wall 120 along one side of the receptacle holder 102. The space between each pair of adjacent divider walls 110 defines a sample receptacle pocket 124, or receptacle-receiving area, for receiving an individual receptacle. In one embodiment, position-identifying indicia, such as barcode 125, is provided on an outwardly-facing panel of the divider walls 110 adjacent each pocket 124. The indicia, which may also include an alphanumeric identifier, "A", "B", "C", etc., uniquely identifies each pocket 124. A machine readable label, such as "empty pocket" barcode 123, may be provided within each pocket 124, on the inner side of surface panel 122 to uniquely identify each pocket and to indicate when a receptacle is not present in the pocket 124.

Figure 4:
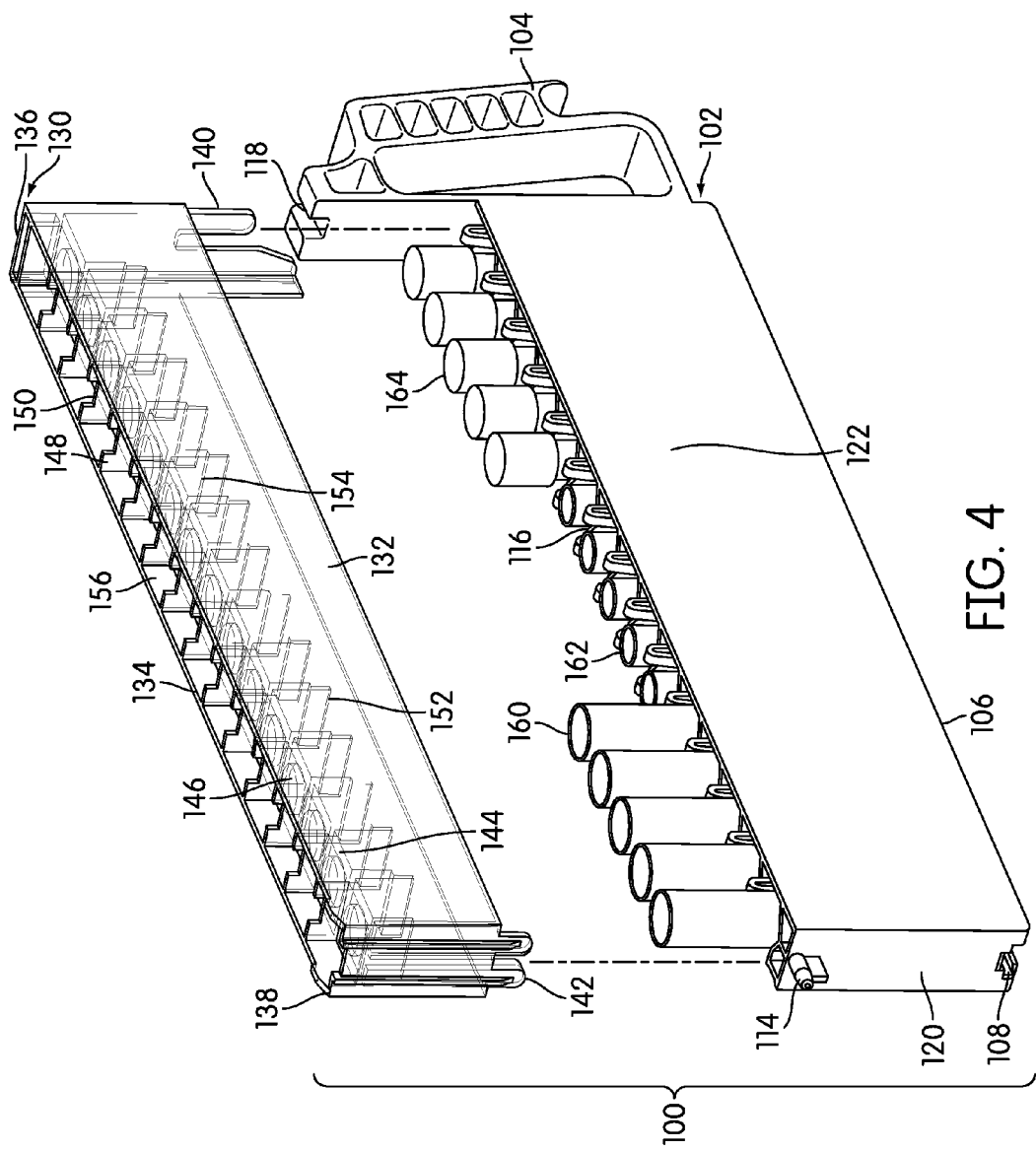
FIG. 4 is a perspective view of a sample rack of the sample receptacle module including a receptacle holder and a cover shown removed from the receptacle holder.
Figure 5:
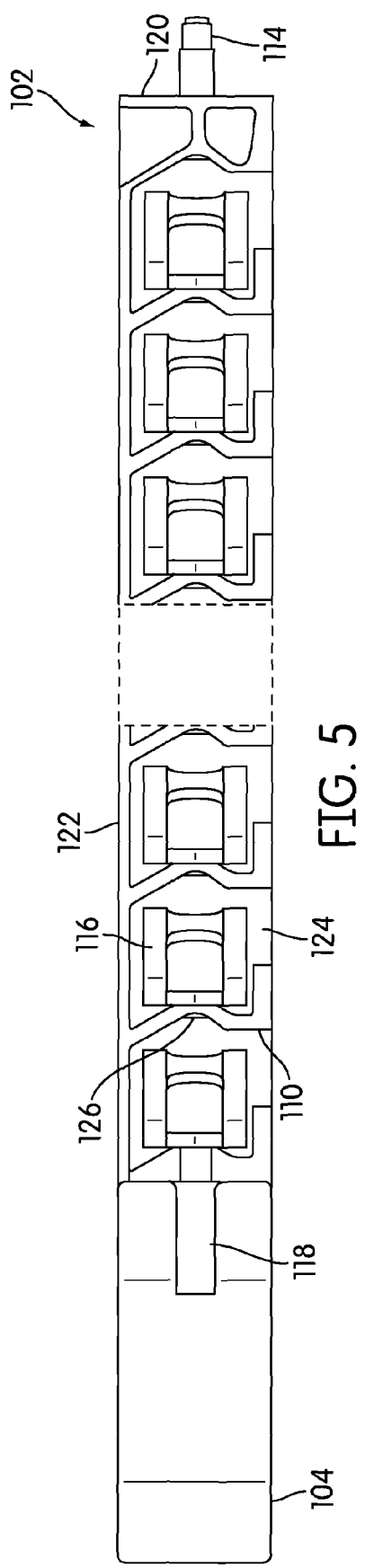
FIG. 5 is a top view of the receptacle holder with the cover removed.
Figure 7:
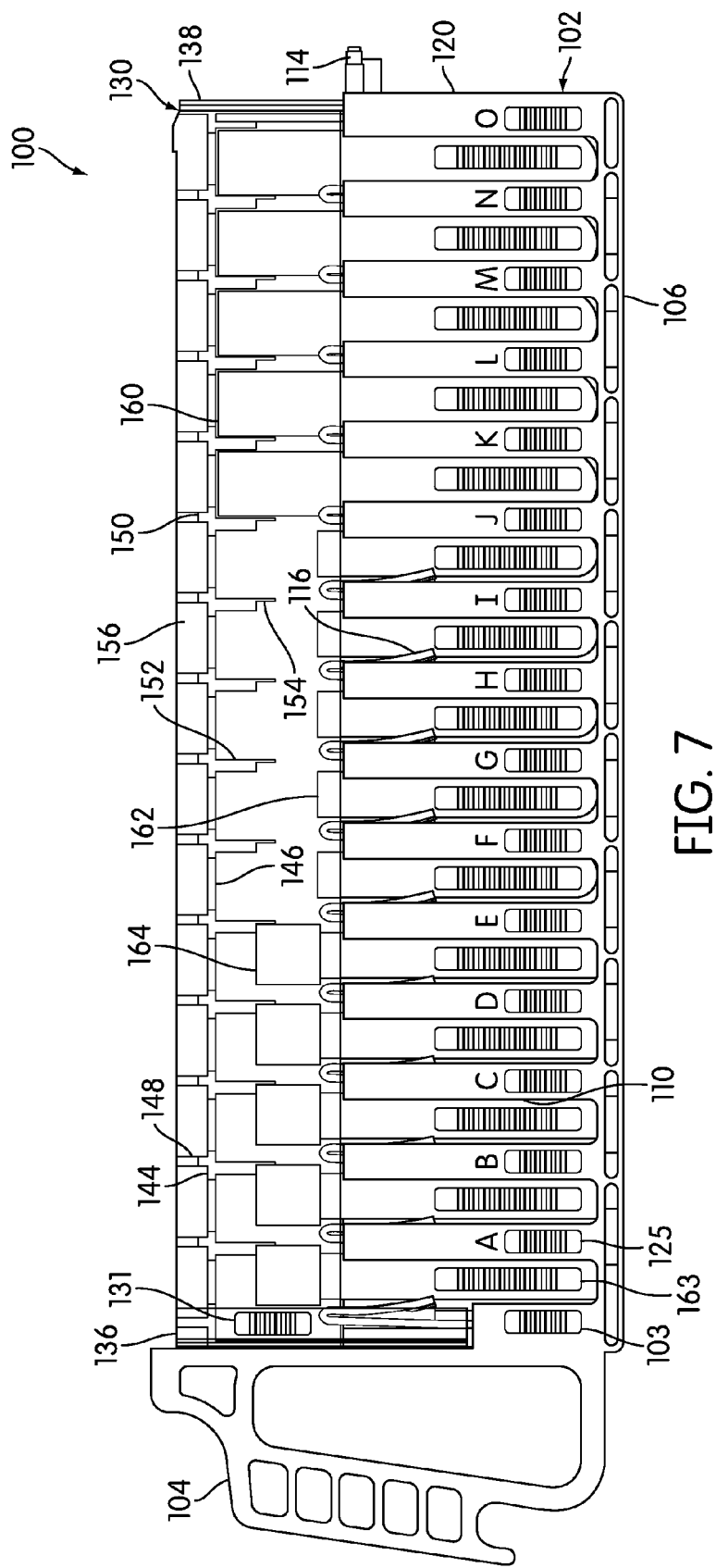
FIG. 7 is side view of the sample rack, including the receptacle holder and the cover, with a plurality of differently-sized sample receptacles carried in the receptacle holder.

A resilient element, such as a spring clip 116, is provided in each sample receptacle pocket 124. Spring clip 116 comprises a bent element (made of, e.g., spring stainless steel) with one portion attached to one divider wall 110 defining a receptacle pocket 124 and another portion extending at an acute angle into the pocket. Each sample receptacle pocket 124 can accommodate receptacles of varying sizes. The receptacle is held in a relatively secure, fixed position within the pocket 124 by means of the spring clip 116 which urges the receptacle toward a divider wall 110 forming one side of the sample receptacle pocket 124. As shown in FIG. 5, each divider wall 110 incorporates a positioning feature, such as a shallow V-shaped notch 126, which assists in positioning (e.g., centering) a receptacle urged against the divider wall 110 by the spring clip 116. FIGS. 4 and 7 show the receptacle holder 102 carrying a plurality of large receptacles 160, small receptacles 162, and medium-sized, capped receptacles 164. In one embodiment, the receptacles are test tubes ranging in size from 12 mm to 16 mm in diameter. It will be apparent to persons of ordinary skill in the art that the dimensions of the receptacle holder 102 can be scaled to accommodate receptacles of different sizes.

Cover 130 fits over the top ends of the sample receptacles projecting above the receptacle holder 102, and is preferably made from a transparent or translucent plastic material so that the contents of the receptacle holder 102 can be observed without removing the cover 130. The cover 130 includes first and second longitudinal side walls 132, 134 and end walls 136, 138. The cover 130 may include structural elements for releasably securing the cover 130 to the receptacle holder 102. In the illustrated embodiment, the cover includes locking forks 140, 142 at opposite ends of the cover 130 (See FIG. 4) which engage mating elements (not shown) formed in the receptacle holder 102 for releasably securing the cover 130 to the receptacle holder 102. In one embodiment, cover 130 includes a machine-readable label, such as barcode 131.

A horizontal transverse wall 144 extends between the side and end walls 132, 134, 136, 138 below the topmost edges of the side and end walls, thereby defining a trough 156 in the upper portion of the cover 130. A plurality of longitudinally-spaced access openings 146 are formed in the transverse wall 144, and upper divider walls 148 extend laterally between the side walls 132, 134 between each of the access openings 146. Each upper divider wall 148 may include a rectangular notch 150 formed in an upper, central portion thereof. Lower divider walls 152 extend laterally between the side walls 132, 134 below the transverse wall 144 at positions between the access openings 146. The space between consecutive lower divider walls 152 is large enough to accommodate the width (e.g., diameter) of the largest receptacle that can be carried in a sample receptacle pocket 124 (see large tubes 160 in FIG. 7). The cover 130 further includes a receptacle-retaining element configured to engage a portion of the top of certain-sized receptacles urged into a centered, or other predetermined, position within each receptacle pocket 124 by the spring clip 116 and the V-shaped notch 126. More specifically, in the illustrated embodiment, each lower divider wall 152 includes a cap notch 154 extending across the divider wall 152 at a lower end thereof. The cap notch 154 accommodates a receptacle cap when the cover 130 is placed over a receptacle holder 102 carrying one or more capped receptacles 164 (see FIG. 7).

Capped receptacles 164 may comprise receptacles provided with a cap that is penetrable by the probe of a fluid transfer mechanism, such as described in U.S. Pat. Nos. 6,893,612 or 7,435,389. The probe penetrates the cap by puncturing one or more pierceable members of the cap as the probe is moved into the receptacle. The cap may also include a filter element through which the probe must pass before reaching a fluid contained within the receptacle 164. After the probe penetrates the cap, friction between the penetrated portions of the cap and/or the filter element and the probe can cause the receptacle 164 to lift out of its pocket when the probe is withdrawn from the receptacle 164. The cap notch 154 of the cover 130 applies a downward holding force on the capped receptacle 164 to prevent the receptacle 164 from being lifted out of the receptacle pocket 124 when a probe that has penetrated the cap is withdrawn from the receptacle 164.

In the illustrated embodiment, an optional home pin 114 extends from the end wall 120. Home pin 114 lets the instrument know that the sample rack has been fully inserted into the sample bay 10, or when it is being removed, for example by extending through holes 19 formed in back wall 18 and engaging a sensor, such as a slotted optical sensor (not shown) mounted to the back wall 18. Home pin 114 may also function as a positioning element to assure the rack is absolutely vertical.

The sample rack 100 is placed within the sample bay 10 by positioning the sample rack 100 in an aligned orientation with respect to the sample rack guides 22 provided on the floor plate 20 of the sample bay 10. As noted, sensors may be provided for detecting the presence of a sample rack 100 and to indicate whether the sample rack 100 is fully inserted into the sample bay 10.

Receptacles are placed in the sample rack so that machine-readable labels (e.g., barcodes 163, see FIG. 7) as well as human-readable labels are visible through the side opening of each pocket 124 between adjacent divider walls 110. As a sample rack 100 is inserted into the sample bay 10, the barcode reader 15 reads each barcode 163 sequentially as the receptacles 160, 162, and/or 164 carried in the receptacle holder 102 pass the barcode window 14. If a pocket 124 is empty, the barcode 123 is read, indicating the absence of a receptacle in the pocket 124. Each position-identifying barcode 125 is also read by the barcode reader 15 to provide pocket identification data with which to associate the receptacle (or absence of a receptacle) carried in the corresponding pocket 124. Preferably only one barcode reader is provided and, therefore, as can be appreciated from FIG. 1, it will be necessary to fill sample rack lanes (defined by the sample rack guides 22) moving from left to right so that there is no carrier between the carrier being inserted and the barcode window 14 and barcode reader 15. Indicator lights at each of the lanes may illuminate sequentially as an indication to the operator as to which lane should be loaded next. The barcode information for each receptacle is stored (e.g., in the memory of an instrument computer controller (not shown)), and that information is correlated with the carrier position (i.e., lane) within the sample bay 10. The barcode reader also reads the receptacle holder barcode 103 to identify the receptacle holder 102 and the cover bar code 131 to ensure that the cover 130 is in place.

Occasionally, receptacles are labeled with barcodes of relatively poor quality that can be read only by a barcode reader that is in relatively close proximity to the barcodes. For such situations, the sample bay 10 and instrument controller preferable provide a "high resolution reading mode" ("HRM"), referred to as the high resolution reading mode because it is in this mode in which the barcode reader 15 can read in the highest resolution (i.e., smallest line size).

HRM is preferably operator-selectable. After HRM is selected, the sample rack 100 loaded with receptacles 160, 162, and/or 164 with barcodes 163 is first inserted in the far right-hand sample rack lane, closest to the barcode reader 15 and window 14 (this will be referred to as the high resolution reading lane). An audible and/or visible indicator may be provided to identify the high resolution reading lane.

As the sample rack 100 is inserted into the high resolution reading lane, each receptacle barcode 163 is read and receptacle data obtained by reading the barcode 163 is stored. Position-identifier barcodes 125 and a receptacle holder barcode 103 are read and stored as well. The pocket-identifier data and the rack-identifier data are associated with the receptacle data obtained for each of the receptacles in the rack, for example in a relational database. The close proximity of the high resolution reading lane to the barcode reader 15 will increase the likelihood of an accurate read.

After the sample rack 100 has been fully inserted into the high resolution reading lane, the sample rack 100 is then withdrawn. A sensor may be provided to sense when the sample rack 100 has been fully inserted, and an indicator light and/or audible tone may signal to the operator that the sample rack 100 may be removed. After the sample rack 100 is removed, it is then re-inserted into one of the other, available lanes. An indicator light may be provided to identify the lane into which the sample rack 100 is to be inserted. As the sample rack 100 is inserted into the available lane, the barcodes 163 on the receptacles are not re-read, but the sample receptacle holder barcode 103 may be read to confirm that the sample rack 100 that was just scanned in the high resolution reading lane is being inserted. The cover barcode 131 may also be read to ensure that the cover 130 is in position. The receptacle data associated in the database with that rack identification then becomes associated with that lane.

The controller may be configured to erase or otherwise disable the barcodes if the sample rack 100 is not re-inserted into an available lane within a specified period of time (e.g., 5 seconds). Thus, if the sample rack 100 is not re-inserted into the sample bay 10 within the specified period of time, the controller will not recognize the sample rack 100 as having been previously scanned in the high resolution reading lane, and the sample rack 100 will have to be scanned in the high resolution reading lane again. This control feature will minimize the ability to switch one or more un-scanned receptacles for scanned receptacles in the time between withdrawing the sample rack 100 from the high resolution reading lane and reinserting the sample rack 100 into another available lane.

Figure 6:
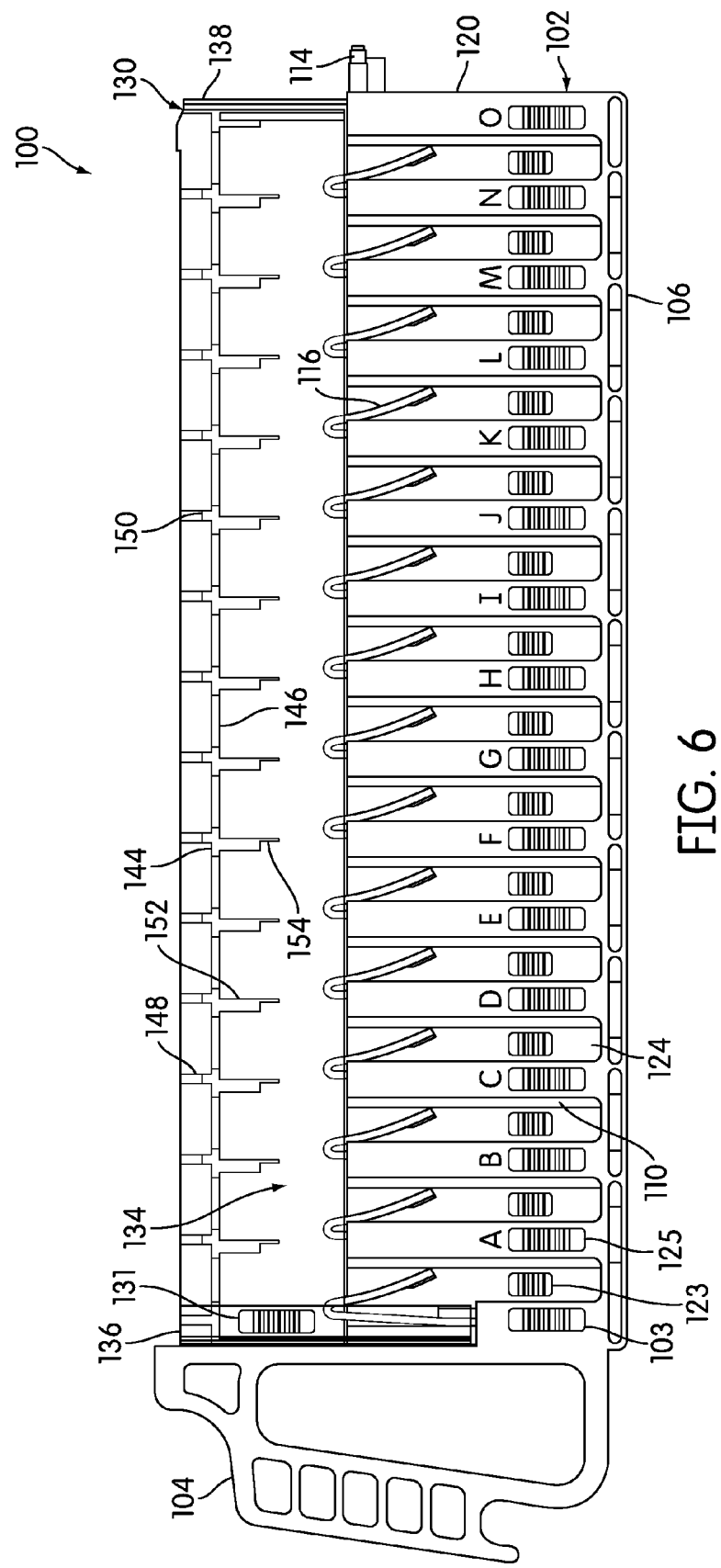
FIG. 6 is a side view of the sample rack, including the receptacle holder and the cover.
Figure 8:
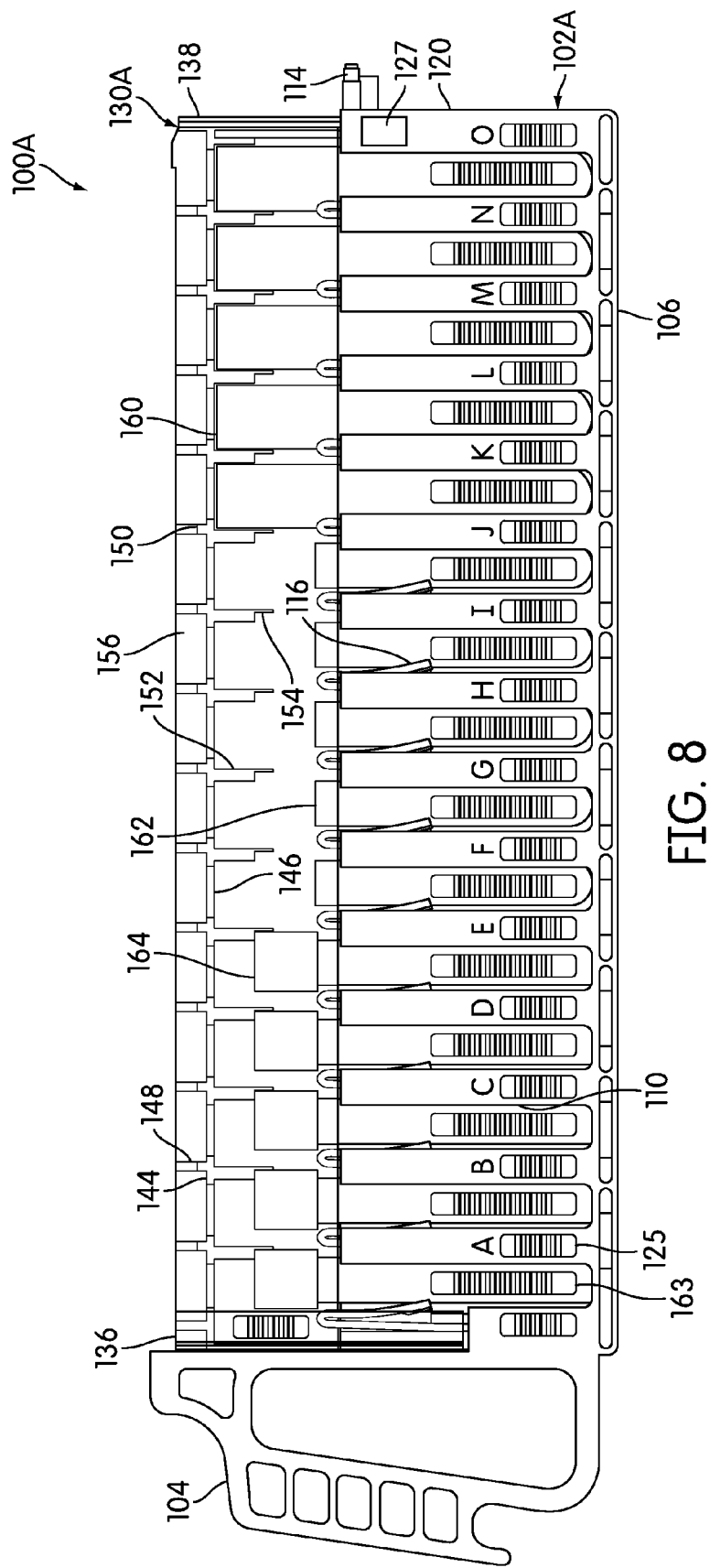
FIG. 8 is a side view of an alternative embodiment of the sample rack, including the receptacle holder and the cover.

An alternative embodiment of a receptacle rack is designated by reference number 100A in FIG. 8. Receptacle rack 100A includes a receptacle holder 102A and a cover 130A. Receptacle rack 100A may be substantially identical to sample rack 100 but includes, instead of or in addition to, receptacle holder barcode 103 and cover bar code 131 (as shown in FIGS. 6 and 7) an electronic memory element 127 to which data can be written and from which data can be read. Memory element 127 may, for example, comprise a radio frequency identification (RFID) tag or a touch memory (or contact memory) element. In one exemplary embodiment, the RFID tag is a high frequency RFID. The RFID can be permanently or removably incorporated onto the receptacle holder 102A (or the cover 130A) in any suitable manner, such as by co-molding, adhesive, potting, etc. Data from the receptacle bar codes 163 and data from the position-identifying bar codes 125 are read by a bar code reader, and data encompassing (or containing) information derived from the bar code data, as well as, optionally, data encompassing other information associated with the bar code information, is written to the memory element 127 to be readable by a processing instrument.

More specifically, a reader station is configured to receive the receptacle rack 100A and includes one or more bar code readers (or other device(s) configured to read machine-readable labels) constructed and arranged to read the receptacle bar codes 163 and the position-identifying bar codes 125 (or other machine-readable labels) and a data writer configured to write data encompassing information derived from the bar code data to the memory element. In one embodiment, the bar code reader is positioned with respect to a rack-receiving location within the reader station to read each bar code 163 and 125 as the receptacle rack 100A is inserted into the reader device. Alternatively, the bar code reader(s) can be mounted to a translating carrier so as to move the reader(s) relative to the stationary bar codes after the receptacle rack is inserted into the reader station. The data from each receptacle bar code 163 is associated with the data of the position-identifying bar code 125 of the pocket 124 in which each of the receptacle (160, 162, or 164) is located. If the pocket 124 is empty, data from an empty pocket bar code 123 is associated with the data of the position-identifying bar code 125 of the empty pocket 124.

The receptacle rack 100A and receptacle holder 102A shown and described are exemplary and are not intended to be limiting. Various arrangements and configurations are contemplated and encompassed within the present disclosure. For example, the receptacle holder may comprise two or more rows (which may or may not be parallel), or other arrangements, of receptacle pockets. A reader station configured to receive a multiple-row receptacle rack would be correspondingly modified to read bar codes, or other machine-readable labels, on the rack and the receptacles carried therein. For example, a reader station configured to receive a receptacle rack comprising two rows of receptacle pockets may include two label reading devices disposed on opposite sides of the rack, each device being configured to read data from the labels on receptacles on the corresponding side of the rack.

In another embodiment, the receptacle rack may carry a combination of labeled and unlabeled receptacles. The labels of the labeled receptacles are read in the reader station and information derived from data read from the labels is written to the memory element, and the unlabeled receptacles are not read. The reader station would not write data regarding the unlabeled receptacles to the memory element, but data containing information relating to the unlabeled receptacles could be written to the memory element, for example, in a non-volatile manner, prior to the receptacle being placed in the reader station. For example, the rack may comprise a pre-assembled kit, with one portion of the rack being devoted to carrying a pre-determined array of reagents and/or other materials for use in performing assays or other processes on samples carried in labeled receptacles placed on another part of the rack. In association with the assembly of the kit, data containing information relating to the predetermined array of materials—e.g., identification and location of the materials—could be written to the memory element. In this regard, one portion of the memory element—or a separate and distinct memory element—may include read-only memory that cannot be written to by the reader station, while another portion of the memory element—or a different memory element on the receptacle rack—includes read-write memory to which the reader station can write data containing information derived from the labeled receptacles.

In one embodiment, the data of the receptacle bar code 163 constitutes an address in a database within which information regarding the contents of the receptacle is stored. For example, if the receptacle is a sample container, the information contained in the bar code 163 data may be used to look up in a database information regarding the sample, such as the nature of the sample (blood, urine, etc), the identity of the patient from whom the sample was obtained, the date the sample was obtained, the test(s) or assay(s) to be performed on the sample, etc. On the other hand, if the receptacle contains reagent or some other process material, information contained in the bar code 163 data may be used to look up in a database information regarding the type of process material, manufacturer, lot number, expiration date, storage conditions, history of use, volume, etc. Data encompassing the information regarding the contents of each receptacle, as well as the location of each receptacle, are then written to the memory element 127. Thus, all data associated with the receptacle rack 100A and the receptacles carried thereon can be stored in one discrete storage medium, namely the memory element 127.

The reader station may include means, such as an audible tone and/or an indicator light, to indicate that the bar code reading and data writing to the memory element 127 has been successfully completed. Alternatively, or in addition, the reader station may send a signal to a CPU 418 to indicate that the bar code reading and data writing to the memory element 127 has been successfully completed. After data is read and written in the reader station, the receptacle rack 100A is removed from the reader station and can be stored for later processing, or it can be transferred directly into a processing apparatus. Within the processing apparatus, a reading element is positioned to read the data stored in the memory element 127, and all the information contained in that data regarding the contents and location of each receptacle within the receptacle rack 100A is communicated to the processing apparatus from the memory element 127.

Figure 9:
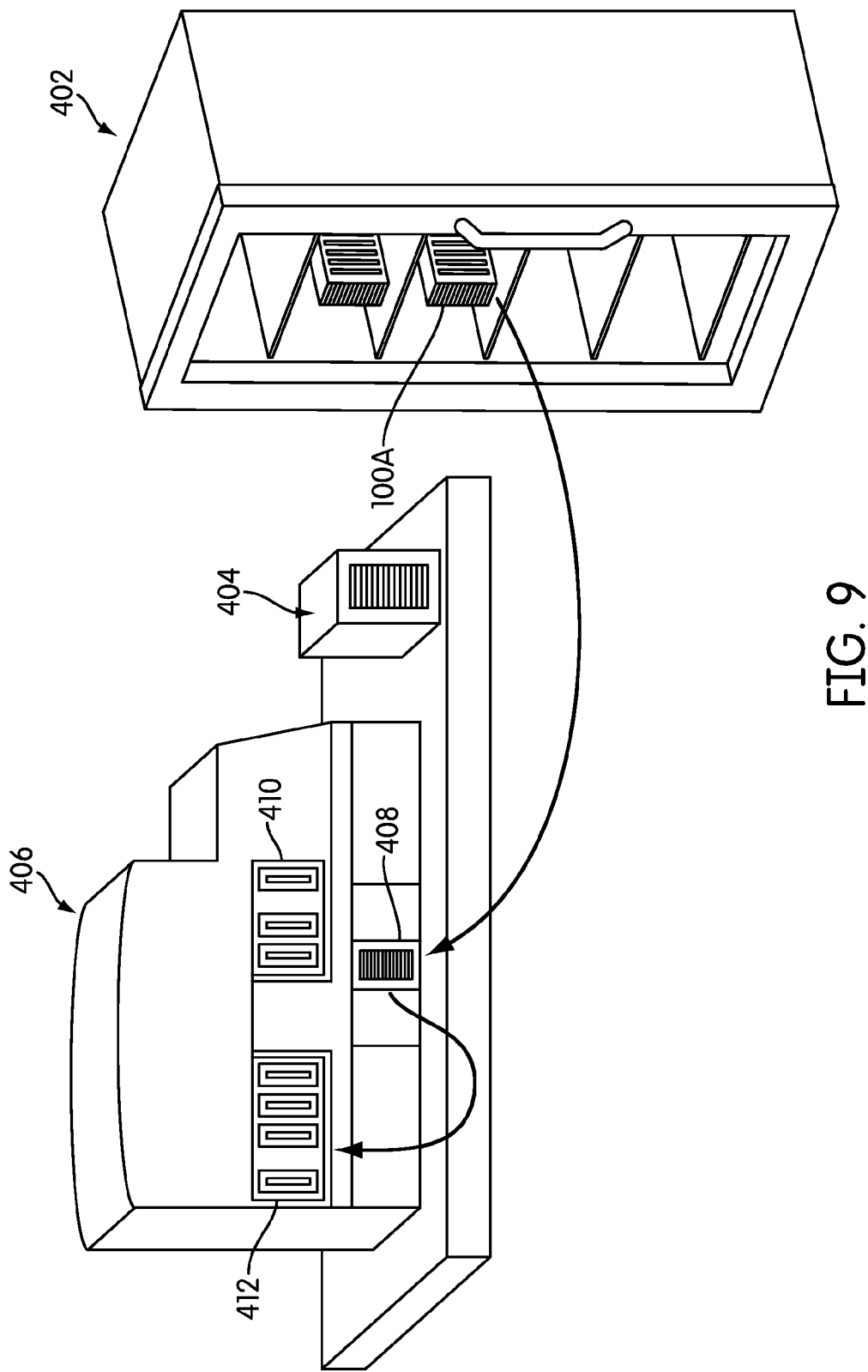
FIG. 9 shows a diagnostic processing system including apparatus for storing receptacle information on a rack holding one or more receptacles and for writing receptacle information to a memory device.

FIG. 9 shows a system in which receptacle rack 100A may be used. The system includes a processing apparatus 406, such as a nucleic acid diagnostic instrument or other sample testing instrument, which may include receptacle slots 412 for receiving receptacle racks 100A holding sample-filled receptacles, and optionally reagent slots 410 for receiving receptacle racks 100A holding reagent-filled containers. In an exemplary implementation, receptacle racks 100A are removed from a storage cabinet 402 (which may be refrigerated) and are inserted, one-by-one, into a reader station in which bar code data on the rack 100A is read and data is written to the memory element 127. The reader station may be an external reader 404 that is remote from the processing apparatus 406, or the reader station may be an integral reader 408 that is part of the processing apparatus 406. Each rack 100A is then removed from the reader station (404 or 408) and then inserted into the appropriate slot (410 or 412) where data from the memory element 127 is read and the contents of the receptacles of the rack 100A are processed according to information contained in, or derived from, that data. Alternatively, the rack 100A can be placed back into the storage cabinet 402—or other storage location—and stored for later processing in the processing apparatus 406.

The use of one or more external reader(s) 404 in combination with one or more processing apparatus(es) 406 is contemplated in the present disclosure. For example, in one embodiment a single external reader 404 is utilized, as noted herein, in combination with multiple processing apparatuses 406. The use of an external reader 404 may provide several advantages. For example, use of an external reader permits reduction in the size of the processing apparatus 404, thus permitting increased available laboratory or bench space. In addition, an external reader can be utilized in conjunction with multiple processing apparatuses, thus providing time, personnel, and/or data management efficiencies.

In one embodiment, the receptacle rack 100A includes a mechanism that reduces the likelihood that the receptacles can be tampered with after the bar codes have been read and data has been written to the memory element 127. This is important in certain embodiments where the rack 100A is placed in the processing apparatus 406 and only the data from the memory element 127 will b read, without reading the receptacle labels (e.g., bar codes) and receptacle position labels (e.g. bar codes). Accordingly, if the receptacles on the receptacle rack 100A placed into the processing apparatus 406 do not correspond to the receptacles and their positions on the rack when the receptacle and position labels were read and the receptacle data and position data was written to the memory element 127 in the reader station 404 or 408, the data on the memory element 127 will not be accurate.

For example, the rack 100A may include a device that erases, scrambles, overwrites, or supplements that data stored on the memory element 127 or otherwise prevents the memory element 127 from being read if the cover 130A is removed from the rack 100A, or if the cover 130A is removed and replaced on the rack 100A without reading or re-reading the data on the rack 100A in the reader station (404 or 408) after the cover 130A is replaced. In another variation, the rack 100A may include a mechanical tamper-prevention flag that is set to a "locked" position when the rack 100A is inserted into the reader device. For example, the reader 404 (or 408) may include a pin, solenoid, or other actuator that engages the tamper-prevention flag—initially in an unlocked position when the rack 100A is first inserted into the reader 404/408—and moves the tamper-prevention flag from the unlocked to the locked position. The tamper-prevention flag will remain in the locked position as long as the cover 130A is not removed from the receptacle holder 102A. The slots 410/412 of the processing apparatus 406 may include a sensor (e.g., an optical sensor) for detecting whether the tamper-prevention flag is in the locked or unlocked position or otherwise determining if the flag is in a position indicating that the rack has not been tampered with after data was written to the memory element 127. If the tamper-prevention flag is in the locked position, data read from the memory element 127 will be accepted, and processing will continue. On the other hand, if the tamper-prevention flag is not in the locked position, data read from the memory element 127 will not be accepted, and processing for that rack 100A will be aborted. This can be implemented by means of data processing software that uses the output of a detector for detecting the position of the tamper-prevention flag as an input that either allows continued data processing or aborts data processing depending on the output of the detector.

Figure 10A:
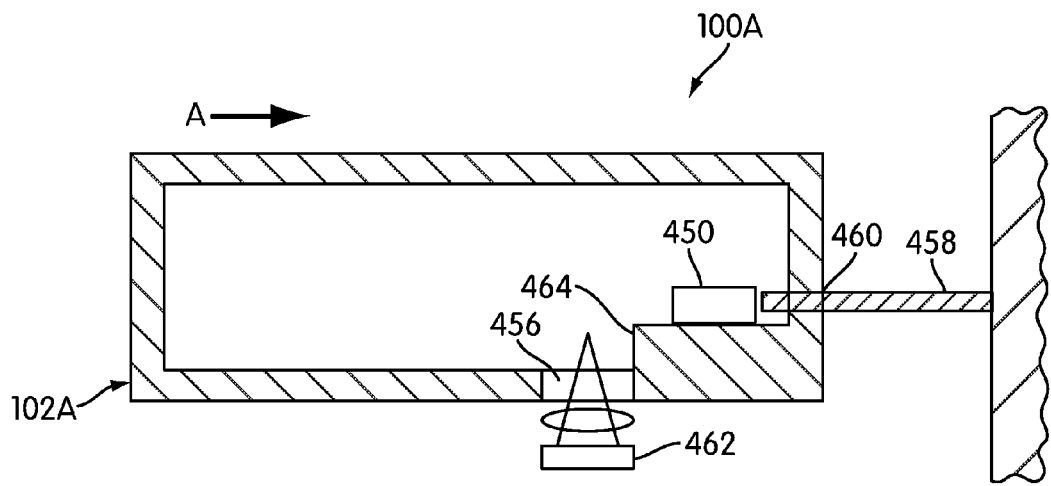
FIGS. 10A-10D show the aspects of an embodiment of a tamper-prevention element.
Figure 10B:
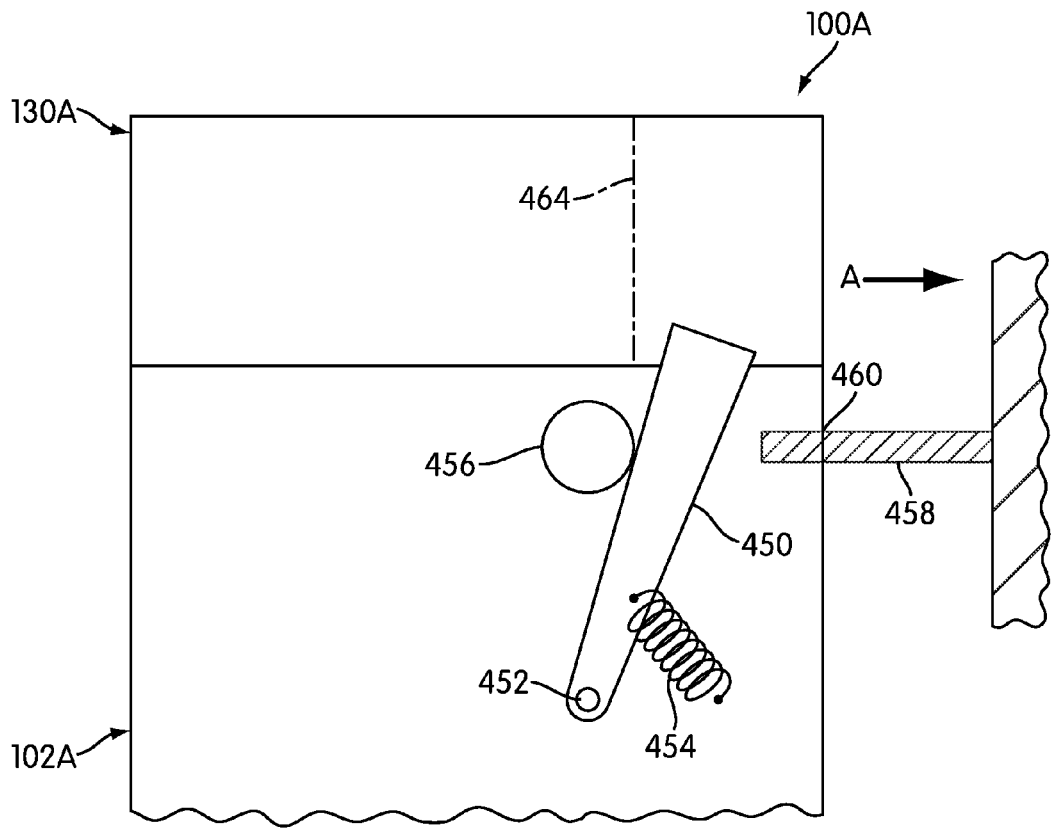
Figure 10C:
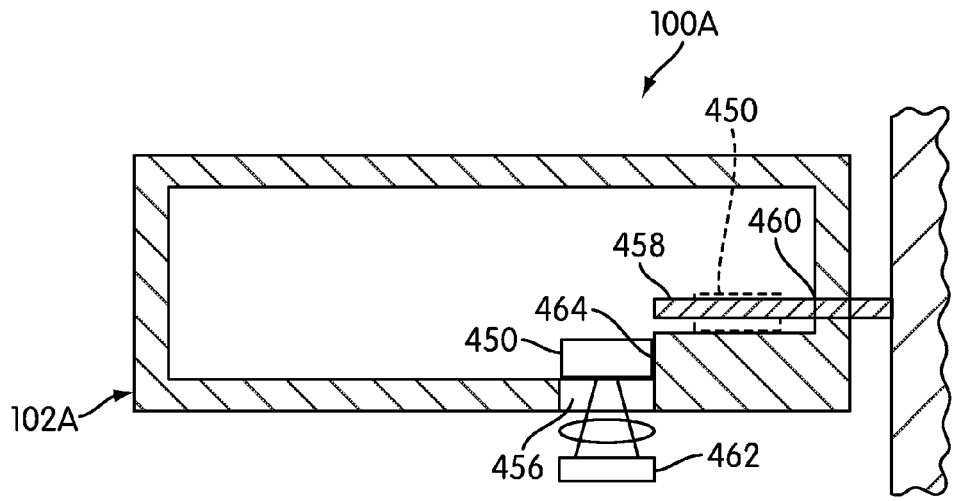
Figure 10D:
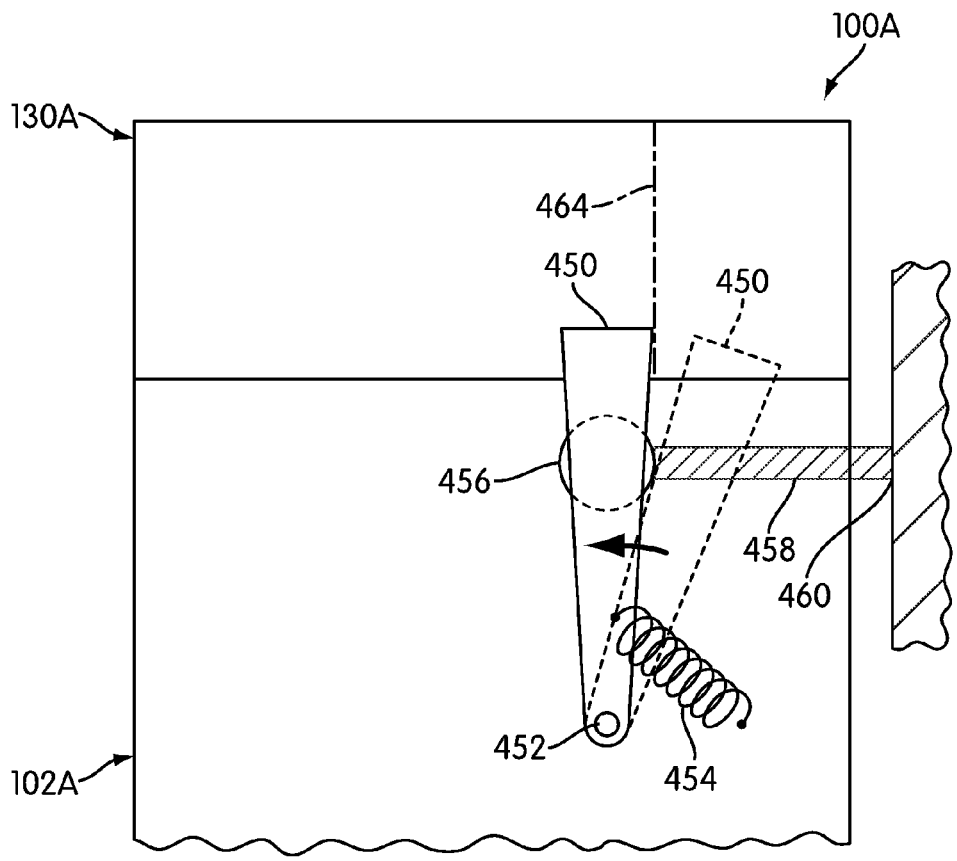

An exemplary configuration of a mechanical tamper-prevention flag is shown in FIGS. 10A-10D. In the illustrated embodiment, a pivoting tamper-prevention flag 450 is mounted to a sidewall of the receptacle holder 102A at pivot pin 452. A spring 454 biases the tamper-prevention flag 450 in a first position shown in FIG. 10B. When the receptacle rack 100A is inserted into an external reader 404 (or an integral reader 408) in the direction "A" shown in FIGS. 10A and 10B, a flag set pin 458 extending from an end wall of the reader 404/408 extends through an opening 460 formed in the receptacle holder 102A. As shown in FIGS. 10C and 10D, the flag set pin 458 engages the tamper-prevention flag 450, and as the rack 100A is inserted into the reader, the flag set pin 458 pivots the tamper-prevention flag 450 against the bias of spring 454 (in a counter-clockwise direction as shown in the figures). When the rack 100A is fully inserted into the reader (i.e., at the position where all the bar codes have been read and the data has been, or will be, written to the memory element 127), the tamper-prevention flag 450 is pushed behind a ridge 464 (or other protrusion) formed on (or attached to) an interior wall of the cover 130A, where the tamper-prevention flag 450 is held in place by means of the spring 454 urging the flag against the ridge 464.

With the tamper-prevention flag 450 in this locked position, as shown in FIGS. 10C and 10D, the flag 450 is disposed in front of an opening 456 formed through a sidewall of the receptacle holder 102A. A sensor 462 disposed adjacent the hole 456 can detect whether or not the tamper-prevention flag 450 is in the locked position. For example, sensor 462 may be a proximity sensor that detects the presence of the tamper-prevention flag 450 in front of the hole 456. In another embodiment, the detector 462 is an optical sensor comprising an emitter and a receiver whereby the path between the emitter and the receiver is blocked by the tamper-prevention flag 450 when the flag 450 is in the locked position in front of the opening 456 as shown in FIG. 10D.

Thereafter, the rack 100A can be removed from the reader 404/408 and inserted into a slot 412/410 of a processing apparatus 406 which will contain a detector, such as detector 462, disposed so as to detect if the tamper-prevention flag 450 is in the locked position in front of opening 456. If, after the tamper-prevention flag 450 is pushed into the lock position by the flag set pin 458, the cover 130A is removed from the receptacle holder 102A, the flag 450 will no longer be held in the locked position behind the ridge 464 and will return to the unlocked position shown in FIG. 10B under the force of the spring 454.

Additional embodiments and configurations of the tamper-prevention element are contemplated. For example, other embodiments of a tamper-prevention element may include (1) a physical element, such as a pin, which breaks, shifts, or deflects if the cover 130A is removed; (2) an electric or electromagnetic element that, for example, breaks a circuit if the cover 130A is removed; or (3) an additional memory element that detects the removal of the cover 130A.

Figure 11:
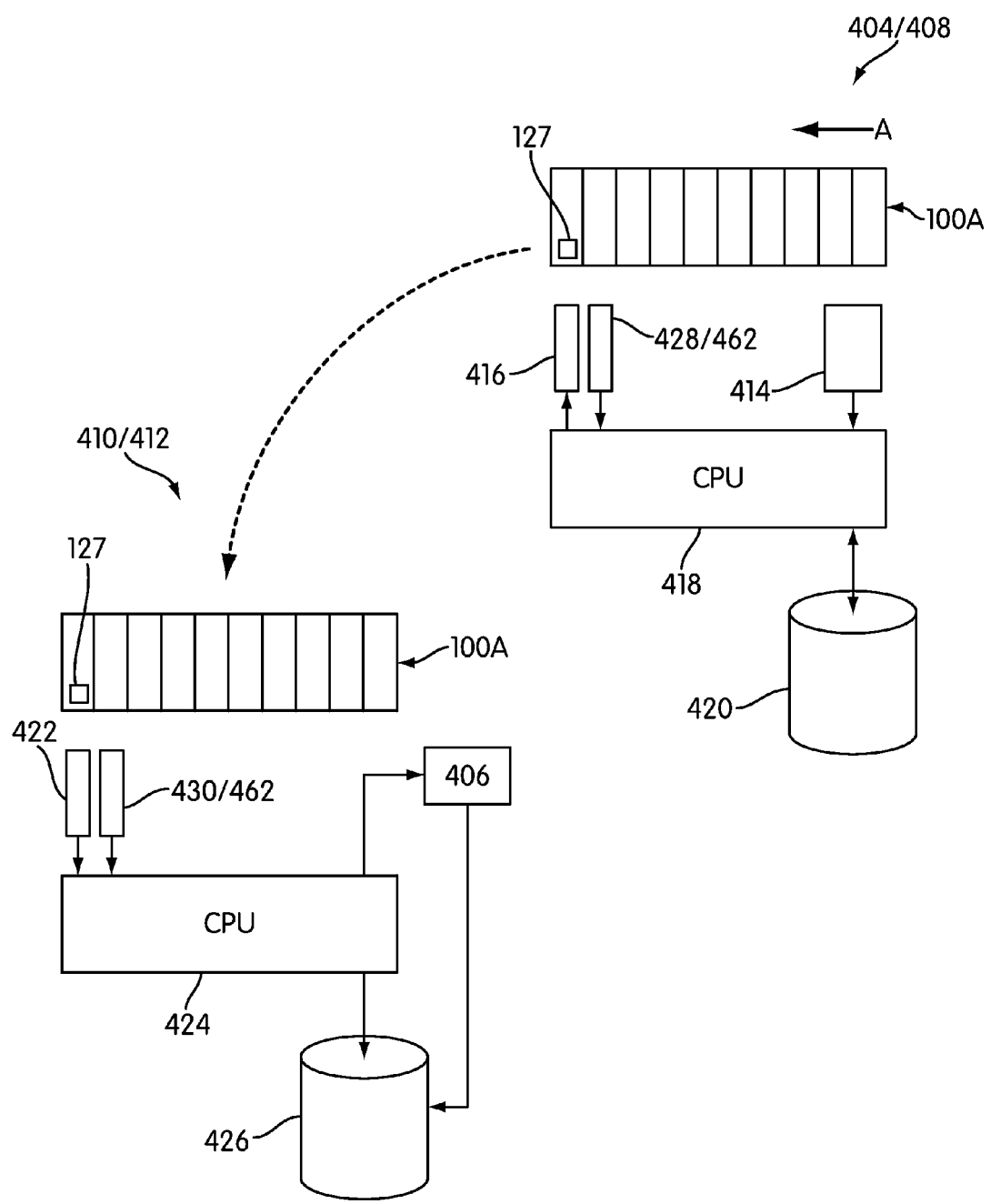
FIG. 11 is a block diagram showing an exemplary system architecture for an embodiment of the invention.
Figure 12:
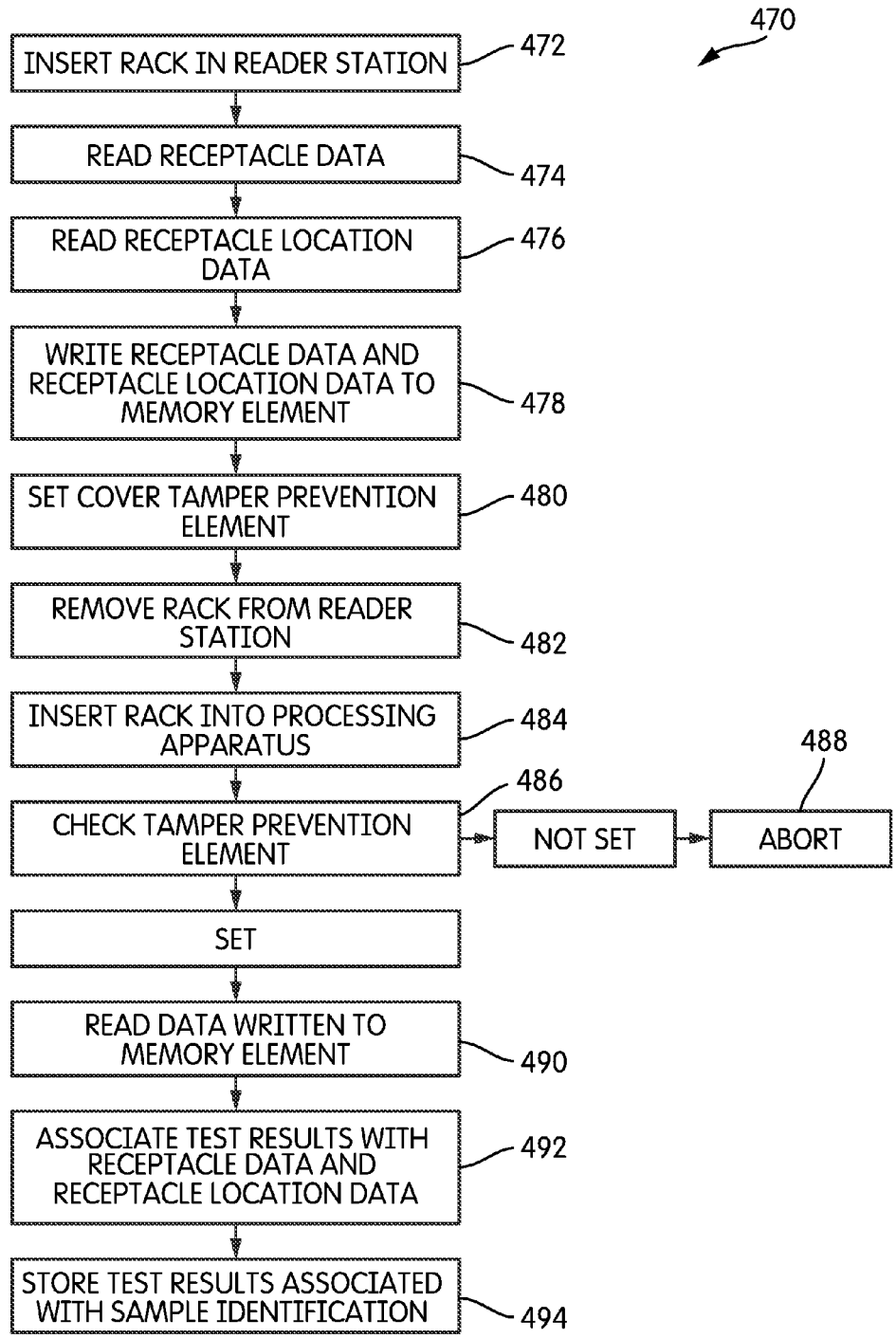
FIG. 12 is a flow chart illustrating a process for reading machine readable labels on the receptacles and the rack and writing data to a memory element on the rack.

FIG. 11 shows exemplary system architecture for implementation of an embodiment of the invention. Operation of the system architecture shown in FIG. 11 will be described in conjunction with FIG. 12, which is a flow chart illustrating a process 470 for reading machine readable labels on the receptacles and the rack and writing data to a memory element on the rack. In the system architecture shown in FIG. 11, a reader station (e.g., an external reader 404 or an integral reader 408) comprises a barcode reader 414 and a memory writer 416 that are in wired or wireless communications with a CPU 418. CPU 418 is a suitable computer apparatus that may or may not be part of and/or in communication with a controller computer that controls operation of the processing apparatus 406. The CPU 418 is in communication with a sample/reagent database 420, which may comprise any suitable electronically-accessible storage media and which stores information regarding samples and/or reagents stored in receptacles carried on a rack 100A. In step 472 of process 470, a rack 100A is inserted into the reader station 404/408, and, in steps 474 and 476, each of the barcodes on the rack 100A (e.g., receptacle barcodes 163, position-identifying barcodes 125, and empty pocket barcodes 123) are read by the barcode reader 414, and the information contained in the barcode data is passed to the CPU 418. Barcode information obtained from receptacle barcodes 163 is used by the CPU 418 to access, from the database 420, sample information regarding each receptacle associated with a barcode, such as the nature of the sample, the identity of the patient from whom the sample was obtained, the date of the sample, the tests or assays to be performed on the sample, etc. As explained above, the barcode data obtained from the receptacle barcode 125 may encompass, or contain, information comprising an address for looking up the associated sample information in a sample file stored in the sample database 420. Alternatively, if rack 100A is a reagent rack, information contained in, or derived from, the data of the receptacle barcode 125 is used by the CPU 418 to access information in the sample/reagent database 420 regarding the nature of the reagent contained within each receptacle.

The information obtained from the data read by barcode reader 414 and the CPU 418, including position-identifying information and sample or reagent information concerning each receptacle carried on the rack 100A, is passed by the CPU 418 to the memory writer 416. In step 478, the data containing information passed to the memory writer 416 is written to a memory element 127 (e.g., an RFID element or a touch memory element). The data written to the memory element 127 can be any data that facilitates retrieval of information corresponding to the receptacles and their locations. For example, data written to the memory element 127 may comprise a memory address in a data file in which detailed information regarding each receptacle and its location is stored. The data written to the memory element 127 may comprise the machine-readable data (e.g., the bar code number) read from each receptacle and the location of each receptacle, and this data may be used to access information relating to each receptacle stored in a database. Alternatively, the data written to the memory element 127 may comprise detailed data regarding each receptacle and its location, thereby limiting or eliminating the need to access such information in another database.

In step 480, a flag set element 428 will set the tamper-prevention flag to the locked position. A detector, such as detector 462, may be provided to confirm that the tamper-prevention flag is in the locked position.

In step 482, the rack 100A is then removed from the reader station 404/408, and, in step 484, the rack is subsequently inserted into a slot 410 or 412 of a processing apparatus 406. The slot 410/412 may also include a tamper prevention element reader 430, which, in one embodiment, includes a detector, such as detector 462, that detects whether the tamper-prevention flag is in the locked or unlock position. Tamper prevention reader 430 is in communication with the CPU 424. The status of the tamper prevention element is checked in step 486. If the tamper prevention element reader 430 communicates to the CPU 424 that the tamper-prevention flag is in the set, or locked, position, data from the memory element 127 is accepted and processing continues. On the other hand, if the tamper prevention element reader 430 communicates to the CPU 424 that the tamper-prevention flag is not in the set, or locked, position, data from the memory element 127 is rejected and processing for that rack 100A is aborted in step 488.

Within the slot 410/412, in step 490, a memory reader 422 reads the data written to the memory element 127. Memory reader 422 is in wired or wireless communication with a CPU 424, which may or may not be the same as CPU 418. CPU 424 is in communication with a results database 426 or other database. CPU 424 may also be in communication with the processing apparatus 406. Data from the memory element 127, as well as data containing information indicating the slot from which the memory element data was obtained, are passed by the CPU 424 to the processing apparatus 406, where the information derived from that data is used for controlling the processing apparatus 406. For example, information regarding the assays to be performed and the reagents contained within the receptacles is passed to the processing apparatus 406 so that the desired assays can be performed on the appropriate samples. In one embodiment, other information obtained from the data read by the memory reader 422 from the memory element 127 is passed by the CPU 424 to the results database 426. The processing apparatus 406 passes test results information data to the results database 426, and in step 492, the test result information is associated with sample identification information obtained from the memory element 127 to generate results data files including sample information and corresponding test results that are stored in step 494. Although FIG. 11 depicts a single processing apparatus 406, the system architecture is capable of supporting multiple processing apparatuses 406 without altering the architecture.

While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the present invention is deemed to include all modifications and variations encompassed within the spirit and scope of the following appended claims.

The invention claimed is:
1. A receptacle rack comprising:
a sample receptacle holding structure defining a plurality of sample receptacle-receiving pockets, each configured to receive and hold a sample receptacle;
machine-readable position data associated with each sample receptacle-receiving pocket and comprising information relating to a position of each sample receptacle-receiving pocket; and
an electronic memory element configured to store information relating to sample receptacles held within receptacle-receiving pockets of the sample receptacle rack and the information relating to a position of each sample receptacle-receiving pocket.
2. The receptacle rack of claim 1, further comprising at least one sample receptacle held within a sample receptacle-receiving pocket, the receptacle including machine-readable sample receptacle data comprising information relating to the contents of the sample receptacle.
3. The receptacle rack of claim 2, wherein the machine-readable receptacle data comprises a bar code disposed on the sample receptacle.
4. The receptacle rack of claim 1, wherein the machine-readable position data comprises a bar code disposed adjacent to each sample receptacle-receiving pocket.
5. The receptacle rack of claim 1, wherein the memory element comprises a radio frequency identification (RFID) tag.
6. The receptacle rack of claim 1, wherein the memory element comprises a touch memory element.
7. The receptacle rack of claim 1, further comprising a cover configured to be removably secured to the receptacle- holding structure so as to cover any receptacle(s) held within receptacle-receiving pockets defined by the receptacle-holding structure.

8. The receptacle rack of claim 2, wherein the machine-readable sample receptacle data comprises information identifying a sample material contained in the sample receptacle.

9. The receptacle rack of claim 2, wherein the machine-readable receptacle data comprises information identifying a reagent contained in the sample receptacle.

10. A receptacle rack comprising:
- a sample receptacle holding structure defining a plurality of sample receptacle-receiving pockets, each configured to receive and hold a sample receptacle;
- an electronic memory element configured to store information relating to sample receptacles held within receptacle-receiving pockets of the sample receptacle rack and the information relating to a position of each sample receptacle-receiving pocket; and
- a tamper prevention element configured to indicate if the cover, once it is secured to the receptacle-holding structure, has been removed from the receptacle-holding structure after the information is stored on the electronic memory element.

11. The receptacle rack of claim 10, wherein the tamper-prevention element comprises an indicator element that is alterable between a first configuration when the cover is secured to the receptacle-holding structure while information is being stored, or has been stored, on the electronic memory element, and a second configuration when the cover is removed from the receptacle-holding structure after the information is stored on the electronic memory element.

12. The receptacle rack of claim 10, wherein the indicator element comprises a movable flag mounted on the cover or the receptacle holding structure to be movable between a locked position and an unlocked position.

13. The receptacle rack of claim 12, further comprising:
- a flag biasing element configured to bias the flag into its unlocked position; and
- flag holding structure configured to hold the flag in its locked position while the cover is secured to the receptacle-holding structure, wherein the flag holding structure is configured such that it will no longer hold the flag in its locked position if the cover is removed from the receptacle-holding structure so that the flag biasing element will cause the flag to return to its unlocked position.

* * * * *